United States Patent [19]

Yamada

[11] Patent Number: 4,605,855
[45] Date of Patent: Aug. 12, 1986

[54] GAS ANALYZER WITH COMPACT CELL STRUCTURE

[75] Inventor: Takeshi Yamada, Kyoto, Japan

[73] Assignee: Horiba, Ltd., Kyoto, Japan

[21] Appl. No.: 644,104

[22] Filed: Aug. 24, 1984

[30] Foreign Application Priority Data

Aug. 30, 1983 [JP] Japan .......................... 58-134971[U]

[51] Int. Cl.[4] ............................................. G01J 1/00
[52] U.S. Cl. ..................................... 250/343; 250/351
[58] Field of Search ........................ 250/343, 373, 351

[56] References Cited

U.S. PATENT DOCUMENTS

| | | | |
|---|---|---|---|
| 3,926,527 | 12/1975 | Pembrook et al. | 250/351 |
| 4,193,695 | 3/1980 | Kojima et al. | 250/351 |
| 4,306,152 | 12/1981 | Ross et al. | 250/343 |
| 4,437,005 | 3/1984 | Ophoff et al. | 250/343 |

*Primary Examiner*—Bruce C. Anderson
*Assistant Examiner*—Richard Hanig
*Attorney, Agent, or Firm*—Wenderoth, Lind & Ponack

[57] ABSTRACT

A gas analyzer has a light source having a window, an open-ended, hollow cylinder aligned with the light source and through which the light from the light source passes, and a detector at the other end of the cell and having a window for receiving the light which has passed through the hollow cylinder. A chopper is provided in the hollow cylinder and is rotatable around an axis perpendicular to the optical path through the hollow cylinder for interrupting the light passing along the optical path. The hollow cylinder has a gas inlet therein at a portion where the optical path for the cell is not screened thereby. The ends of the hollow cylinder are adjacent the light source window and the detector window which serve as cell windows, respectively, at least one of these windows being spaced from the end of the hollow cylinder to define a gap therebetween constituting a gas outlet.

6 Claims, 5 Drawing Figures

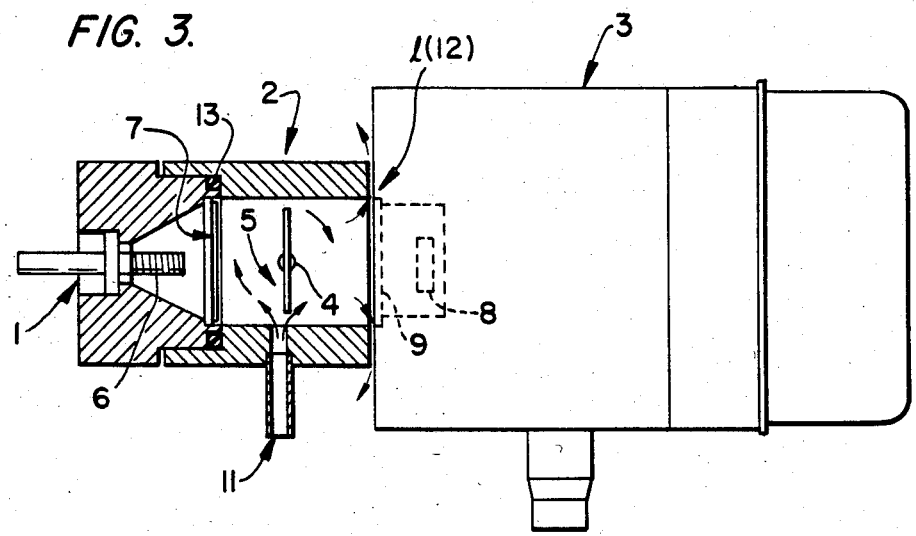
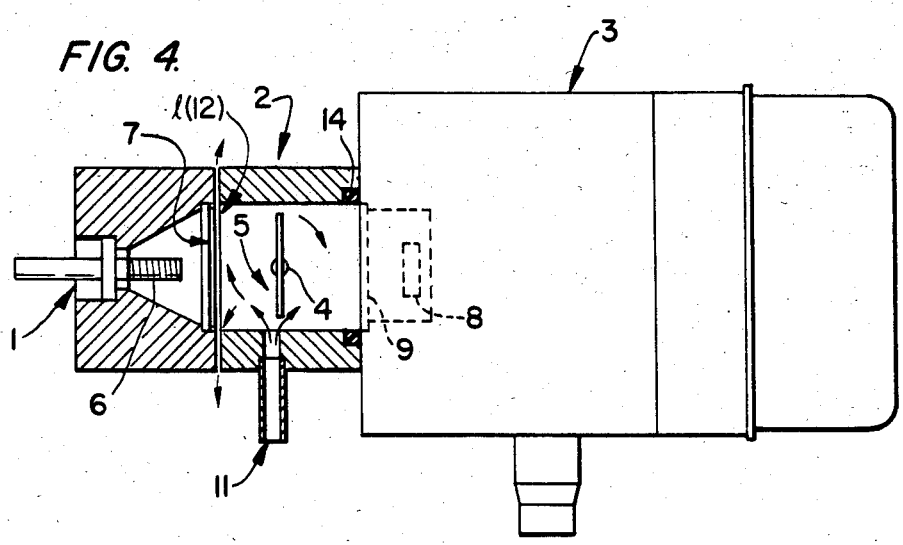
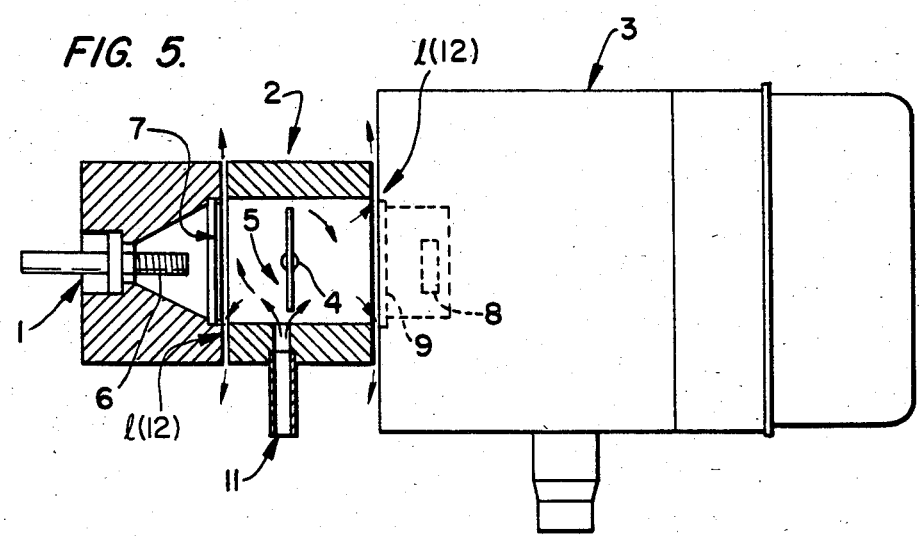

GAS ANALYZER WITH COMPACT CELL STRUCTURE

BACKGROUND OF THE INVENTION

1. Field of the Invention

This invention relates to an improvement in a single beam type infrared gas analyzer which has a light source, a cell through which the light from the light source passes, and a detector receiving the light which has passed through the cell, positioned in series with each other, and a chopper for interrupting the light along the optical path thereof.

2. Description of the Prior Act

A single beam type non-dispersive infrared gas analyzer generally used as this kind of gas analyzer is shown in FIG. 1. This analyzer has a light source 21, a cell 22, a chopper 23 and a detector 24 in series in the recited order, and the cell is provided with a gas inlet 25 and a gas outlet 26 in portions of cell 22 which will not block the optical path of the light therethrough. This type of analyzer is defective in the following ways.

Specifically, dead spaces a, b and c are formed between the light source 21 and the cell 22, the cell 22 and the chopper 23, and the chopper 23 and the detector 24, respectively, so that gas existing in the spaces a, b and c creates a background effect and causes deterioration of measurement accuracy. Moreover, four windows 27 are provided along the optical path, each causing some loss of light energy.

Furthermore, gas containing the component to be measured will tend to flow in the shortest path from the gas inlet 25 to the gas outlet 26, and gas flow at the corners of cell 22 and at the cell windows 27 is slow, so that much time is required for displacement of all of the gas in the cell. Such a problem will also occur in a double beam type analyzer.

SUMMARY OF THE INVENTION

An object of the invention is to provide an extremely simple yet effective improvement in a single beam type infrared gas analyzer.

This object is achieved by the provision of a gas analyzer comprising: a light source having a window; an open-ended, hollow cylinder aligned with said light source and through which the light from said light source passes; a detector at the other end of said cell and having a window for receiving the light which has passed through said hollow cylinder; a chopper in said hollow cylinder and rotatable around an axis perpendicular to the optical path through said hollow cylinder for interrupting the light passing along said optical path; said hollow cylinder having a gas inlet therein at a portion where the optical path for said cell is not blocked thereby; the ends of said hollow cylinder being adjacent the light source window and the detector window which serve as cell windows, respectively, at least one of said windows being spaced from the end of said hollow cylinder to define a gap therebetween constituting a gas outlet.

Other objects and features of the invention will become apparent from the following description of a preferred embodiment, taken with reference to the accompanying drawings.

BRIEF DESCRIPTION OF THE DRAWINGS

FIGS. 3–5 are views similar to FIG. 2 showing further embodiments.

DESCRIPTION OF THE PREFERRED EMBODIMENTS

Figure 1:
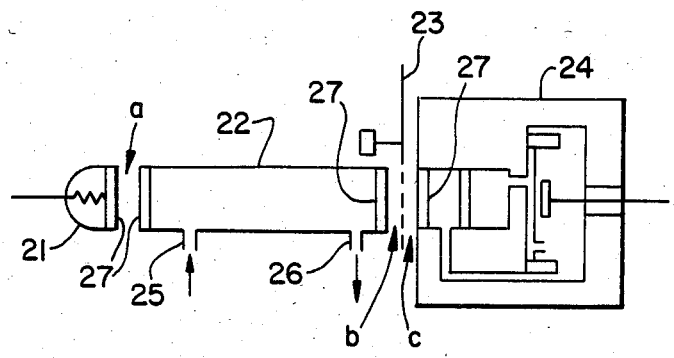
FIG. 1 is a schematic longitudinal sectional view of a conventional single beam type infrared gas analyzer.
Figure 2:
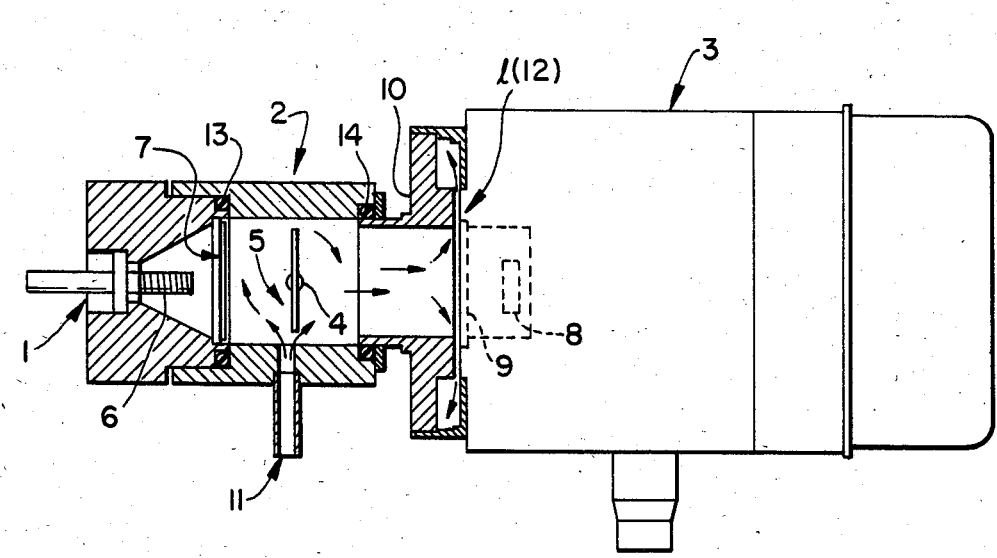
FIG. 2 is a schematic longitudinal sectional view of a single beam type infrared gas analyzer according to the present invention.

Referring to FIG. 2, the single beam type infrared gas analyzer of the present invention has a light source 1, a sample cell 2 aligned with the light source and through which the light from the light source 1 passes, and a detector 3 for detecting the light which has passed through the cell 2, said components being in series. The cell 2 has a chopper 5 therewithin for interrupting the optical path and which is rotatable around a shaft 4 perpendicular to the optical path.

The light source 1 is provided with a light-emitter 6 and a window 7. The cell 2 is a simple, hollow cylinder open at both ends and has one end fitted onto the light source 3 and sealed relative thereto by the seal 13. The detector 3 is provided with a light receiver 8 and a window 9, and has a cylinder 10 on the end toward cell 2 mounted so as to be slightly spaced from detector 3 to define a narrow gap l with respect to window 9. The detector is otherwise conventional. The other end of the cell 2 is fitted onto the cylinder 10 and sealed with a seal 14, so that cylinder 10 forms a continuation of cell 2. Cell 2 is provided at a position which does not block the optical path with an inlet 11 for gas containing a component to be measured.

Thus, the window 7 on the light source 1 and window 9 of the detector 3 also serve as cell windows at the respective ends of cell 2. At least some of the gas from the inlet 11 flows along the window surface of window 7, then along the cell with the remainder of the gas, and is then discharged from cell space, through the gap l, which constitutes a gas outlet 12. In the course of such flow, it flows over the window 9.

In the cell 2, the chopper 5 rotates around the shaft 4 perpendicular to the optical path to produce AC optical signals, and at the same time acts like an impeller to cause the gas in the cell to flow positively toward the outlet and be discharged along the surface of window 9. Hence, gas displacement is performed in a short time, and the gas does not remain in the cell very long.

The cylinder 10, which is used as an intermediate member between the cell and the window 9 of the detector, may be omitted, and the gas outlet 12 formed between the cell 2 itself and the window 9 as shown in FIG. 3. In this arrangement, the window 9 is also used as the cell window. Also, the gas outlet 12 may be formed between the window 7 of the light source and the cell 2, as shown in FIG. 4, or at both ends of cell 2, as shown in FIG. 5.

Also, the present invention is applicable to a double beam type analyzer.

As seen from the above, this invention is characterized in that the aforesaid gas analyzer which has the light source, cell and detector arranged in series and has the chopper in the cell and has a gas inlet at a portion where the optical path is not screened. The chopper is rotatable around a shaft perpendicular to the optical path. The cell uses the window of the light source and of the detector as the cell windows, and a narrow gap is provided between at least one window and the cell space to form the gas outlet.

Thus, the windows of the light source and the detector are used as the cell windows respectively, and dead space is all but eliminated between the light source and the detector, so that no disturbance is caused by gas other than in the cell to thereby lead to a remarkable improvement in measuring accuracy.

The use of the windows of the light source and detector as the cell windows also avoids two windows in the optical path, thereby reducing the light energy loss.

Furthermore, the chopper is provided in the cell both for interrupting the light passing through the cell, but also causing the gas in the cell to flow positively for exhausting it from the interior of the cell along a cell window. Hence, the gas displacement is performed quickly without gas remaining in the cell very long. This simple construction has thus made possible the attainment of the object of the invention.

While a preferred embodiment of the invention has been described using specific terms, such description is for illustrative purposes only, and it is to be understood that changes or variations may be made without departing from the spirit or scope of the following claims.

What is claimed is:

1. A gas analyzer comprising: a light source having a window; an open-ended, hollow cylinder aligned with said light source and through which the light from said light source passes; a detector at the other end of said cell and having a window for receiving the light which has passed through said hollow cylinder; a chopper in said hollow cylinder and rotatable around an axis perpendicular to the optical path through said hollow cylinder for interrupting the light passing along said optical path; said hollow cylinder having a gas inlet therein at a portion where the optical path for said cell is not blocked thereby; the ends of said hollow cylinder being adjacent the light source window and the detector window which serve as cell windows, respectively, at least one of said windows being spaced from the end of said hollow cylinder to define an annular gap therebetween constituting a gas outlet for causing gas leaving the cell to flow out through the end corner of the cell adjacent said one window.

2. A gas analyzer as claimed in claim 1 in which both of said windows are spaced from the respective ends of said hollow cylinder for defining a gap at each end of said hollow cylinder.

3. A gas analyzer as claimed in claim 1 in which said gap is between said light source window and said hollow cylinder, the other end of said hollow cylinder being sealed to said detector.

4. A gas analyzer as claimed in claim 1 in which said gap is between said detector window and said hollow cylinder, the other end of said hollow cylinder being sealed to said light source.

5. A gas analyzer as claimed in claim 4 further comprising a cylindrical member having one end mounted on said detector and spaced from the detector window to define said gap, and the other end being sealed to said hollow cylinder.

6. A gas analyzer as claimed in claim 3 further comprising a cylindrical member having one end mounted on said detector and spaced from the detector window to define said tap, and the other end being sealed to said hollow cylinder.

* * * * *